US006812251B2

(12) United States Patent
Calabresi et al.

(10) Patent No.: US 6,812,251 B2
(45) Date of Patent: Nov. 2, 2004

(54) TAURINE COMPOUNDS

(75) Inventors: Paul Calabresi, Barrington, RI (US); Bai-Chuan Pan, Providence, RI (US); James Darnowski, Barrington, RI (US)

(73) Assignee: Rhode Island Hospital, Providence, RI (US)

( * ) Notice: Subject to any disclaimer, the term of this patent is extended or adjusted under 35 U.S.C. 154(b) by 0 days.

(21) Appl. No.: 10/098,815

(22) Filed: Mar. 15, 2002

(65) Prior Publication Data

US 2002/0183286 A1 Dec. 5, 2002

Related U.S. Application Data

(60) Provisional application No. 60/276,153, filed on Mar. 15, 2001.

(51) Int. Cl.[7] .................. A61K 31/18; A61K 31/16; A61K 31/15
(52) U.S. Cl. ............... 514/601; 514/579; 514/664; 514/665
(58) Field of Search .................. 514/601, 579, 514/664, 665, 707, 708, 709, 711, 365–371, 602, 603, 604; 562/104; 552/1

(56) References Cited

U.S. PATENT DOCUMENTS

| 4,259,332 A | * | 3/1981 | Passoni et al. ............. 424/230 |
| 4,840,964 A | | 6/1989 | Di Schiena et al. ........ 514/448 |
| 5,601,806 A | * | 2/1997 | Katsumata et al. ........... 424/59 |
| 5,869,532 A | | 2/1999 | Mizushima et al. ........ 514/625 |
| 5,889,183 A | * | 3/1999 | Herdeis et al. ............... 544/8 |
| 5,954,687 A | | 9/1999 | Baudino |
| 5,976,822 A | | 11/1999 | Landrum et al. |
| 6,096,536 A | | 8/2000 | Knight et al. ............... 435/325 |

FOREIGN PATENT DOCUMENTS

| WO | WO 96/34854 | * 11/1996 | ......... C07C/311/49 |
| WO | WO 99/35146 | * 7/1999 | ......... C07D/471/04 |
| WO | WO 99/42099 | 8/1999 | |

OTHER PUBLICATIONS

CA:129:95491 abs of WO 9827061 Jun. 1998.*
CA:131:102288 abs of WO9935146 Jul. 1999.*
CA:119:234019 abd of DE 4244090 Aug. 1993.*
The Mereck Index, An Encyclopedia of Chemicals, Drugs, and Biologicals, 10th Edition, 1983, p. 1304.

* cited by examiner

Primary Examiner—Shengjun Wang
(74) Attorney, Agent, or Firm—Ingrid A. Beattie; Mintz, Levin, Cohn, Ferris, Glovsky and Popeo, P.C.

(57) ABSTRACT

The invention provides a method of inhibiting tumor growth by contacting the tumor with a composition containing a taurine compound. The composition is administered to directly contact a tumor cell at a dose sufficient to induce cell death.

2 Claims, 6 Drawing Sheets

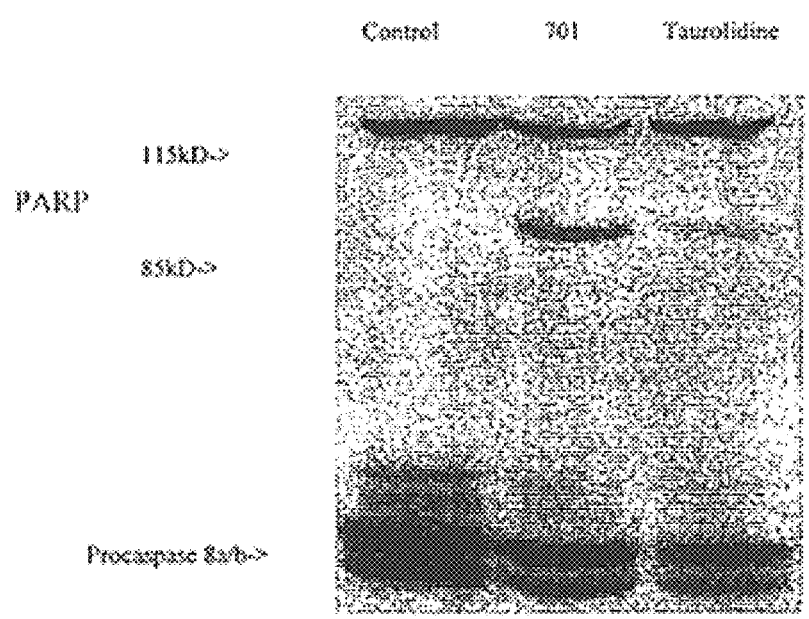

TAURINE COMPOUNDS

This application claims priority to provisional application U.S. Ser. No. 60/276,153, filed on Mar. 15, 2001, the entire contents of which is hereby incorporated by reference.

BACKGROUND OF THE INVENTION

The invention relates to cancer therapy.

Despite advances in the identification of chemotherapeutic agents for inhibiting the growth of cancer cell, cancer remains a formidable disease with a high mortality rate. A significant problem of chemotherapeutic agents is low specificity. Many anticancer agents do not adequately distinguish normal cells from cancer cells. As a result, they often carry undesirable serious side effects.

SUMMARY OF THE INVENTION

The invention provides a method of inhibiting tumor growth in a mammal with few or no deleterious side effects. For example, the method is carried out by administering to the mammal composition containing a non-naturally-occurring taurine compound. For example, the compound is chemically synthesized. A taurine compound is a composition, which contains a taurine moiety (S—C—C—N) but is not a metabolite of taurolidine or taurultam. Preferably, the compound does not contain a methylol moiety, nor does it produce a methylol moiety in an aqueous environment. A taurine compound contains a S—C—C—N backbone but differs from naturally-occurring taurine in that at least substituent is altered compared to naturally-occurring taurine. The compound does not contain an ring structure or an aromatic group, i.e., it is acyclic. For example, the S—C—C—N backbone is not part of a ring structure. Alternatively, the compound contains at least one aromatic group. The compounds differ from taurine by the addition of a substituent (e.g., an azide substituent) on a sulfur or by the addition of a substituent on a nitrogen in the backbone structure. For example, the hydrogens of an amine group are replaced with nitrogens, resulting in the substitution of an amine group with an azide group.

Tissue containing a tumor is contacted (in vivo or ex vivo) with a composition containing a taurine compound. The compound is administered directly or indirectly to contact a tumor cell at a dose sufficient to inhibit growth of tumor cells and/or induce cell death. Preferably the compound is administered in a manner and at a dose which preferentially induces apoptotic death of tumor cells compared to non-tumor (i.e., normal) cells. The compound inhibits proliferation of tumor cells. Preferably the taurine compound is characterized as having a $R_1$—$CH_2$—$CH_2$—$SO_2$—$R_2$ backbone in which $R_1$ and $R_2$ are, independently, an alkyl, aryl, hetero group, or hydrogen.

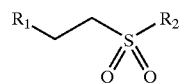

For example, compound is a sulfonamide derivative. Most preferably the compound is an azide derivative, such as β-Azidoethanesulfonyl azide (BC-701). Preferably, the compound is not taurolidine or taurultam.

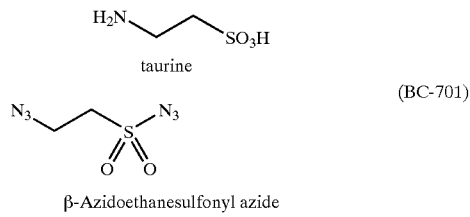

A sulfonamide compound is one having a $R_2N$—$SO_2R'$ formula, an azide compound is one having an $N_3$ formula. The compounds described herein differ structurally from taurine or taurinamide. The compounds have reduced toxicity, prolonged clinical half-life, or improved ability to cross the blood-brain barrier.

The compounds are cytotoxic; the level of cytotoxicity is at least 20% that of taurolidine. Preferably, the compound has at least 40%, 50%, 75%, 85%, 95%, 99% or 100% of the cytotoxic activity of taurolidine. In some cases, the cytotoxic activity of the compound exceeds the level of activity of taurolidine. Cytotoxicity is measured using a variety of standard methods, e.g., detecting the level apoptosis in a treated cell population by flow cytometry or Western blot analysis.

The compounds are antibacterial; the level of antibiotic activity is at least 20% that of taurolidine. Preferably, the compound has at least 40%, 50%, 75%, 85%, 95%, 99% or 100% of the antibiotic activity of taurolidine.

A method of treating an autologous tumor, e.g., a tumor of the central nervous system (CNS), is carried out by contacting a mammalian tumor cell with a taurine compound. For example, the compound is administered to a mammal, e.g., a human patient,. Tumors to be treated include solid tumors, non-solid tumors, and lymphomas. For example, the autologous tumor is a breast cancer, ovarian cancer, colon cancer, prostate cancer, pancreatic cancer, CNS cancer, liver cancer, lung cancer (e.g., mesothelioma), urinary bladder cancer, lymphoma, leukemia, or sarcoma. Tissue containing a tumor is directly or indirectly contacted with the compound., e.g., the compound is administered locally into a tumor site or is administered systemically to the animal.

For tumors of neurological origin, the compound is administered systemically, e.g., orally or intravenously, or infused directly into the brain or cerebrospinal fluid. Other means of drug delivery include an erodible or resorbable solid matrix such as a wafer or sponge, which is implanted directly into brain tissue. Preferably, the tumor is a glioma, astrocytoma, neuroblastoma, or CNS metastasis from a non-CNS primary tumor.

The taurine compound is administered alone or in combination with a second antineoplastic agent. For example, an antimetabolite, a purine or pyrimidine analogue, an alkylating agent, crosslinking agent (e.g., a platinum compound), intercalating agent, and/or an antibiotic is administered in a combination therapy regimen. The coadministered drug is given before, after, or simultaneously with the taurine compound. An advantage of such a combination therapy approach is that a lower concentration of the second neoplastic is required to achieve tumor cell killing.

The invention also includes treating a drug resistant tumor, e.g., a multiple drug resistant (MDR) tumor, in a mammal by administering to the mammal a taurine compound. The tumor to be treated is a carcinoma or sarcoma. The drug resistant tumor is selected from the group consisting of a solid tumor, a non-solid tumor, and a lymphoma. For example, the drug resistant tumor is a breast cancer, ovarian cancer, colon cancer, prostate cancer, pancreatic cancer, CNS cancer, liver cancer, lung cancer, urinary bladder cancer, lymphoma, leukemia, or sarcoma.

Any neoplastic cell can be treated using the methods described herein. Preferably, the taurine compound, e.g., β-Azidoethanesulfonyl azide, is administered in a manner which allows direct contact of the surface of the tumor cell with the compound. Tumors to be treated include but are not limited to leukemia, lymphoma, breast cancer, ovarian cancer, colon cancer, prostate cancer, pancreatic cancer, CNS cancer, liver cancer, lung cancer, gastric cancer, esophageal cancer, urinary bladder cancer, sarcoma, and melanoma. For example, bladder cancer is treated by inflating the bladder with a solution containing a taurine compound, and skin cancers such as basal cell carcinomas or squamous cell carcinomas are treated by applying a taurine compound formulated as a film, cream, or ointment, directly to the affected skin area. For treatment of primary liver cancers or liver metastases, the compounds are infused into the hepatic artery, portal vein, or other blood vessel of the liver. Alternatively, slow release of the compound to any tissue is accomplished by implanting a drug loaded matrix in direct contact or adjacent to the tumor site.

To purge a mixed population of cells, e.g., a patient derived sample of bone marrow cells or peripheral blood cells, of contaminating cancer cells, the bone marrow cells or peripheral blood cells are cultured in the presence of a taurine compound such as β-Azidoethanesulfonyl azide. The ex vivo treated cells are then washed and expanded in culture or infused into a mammalian recipient. e.g., the individual from which the cells were derived or another mammalian recipient. The number of tumor cells in the mixed population is reduced by at least one, preferably at least two, more preferably at least three, more preferably at least four, and most preferably at least five log units, after treatment.

The taurine compounds are formulated for administration to directly contact cancer cells, e.g., in the form of an aqueous solution. Formulations include a therapeutic film-forming composition containing or coated with a taurine compound as well as ointments, pastes, sprays, patches, creams, gels, sponges, and foams.

Other features and advantages of the invention will be apparent from the following detailed description and from the claims.

BRIEF DESCRIPTION OF THE DRAWINGS

FIG. 3 is a photograph of proteins from whole cell lysates of human prostate tumor cell populations, which were contacted with taurolidine, BC-701, or neither compound (control). Total proteins from whole cell lysates were separated by electrophoresis, transferred to nitrocellulose filters, and the filters probes with antibodies that detect markers of apoptotic death.

DETAILED DESCRIPTION

The compounds of the invention are derivatives of the amino acid, taurine. The compounds are not naturally-occurring and are not metabolites or molecular variants of taurolidine or taurultam. Like Bis-(1,1-dioxoperhydro-1,2,4-thiadiazinyl-4)methane (Taurolidine; TAUROLIN™), the compounds function to preferentially induce death of tumor cells compared to non-tumor cells.

Functional Characterization of Taurolidine

The antibiotic activity of taurolidine depends upon a chemical reaction secondary to the generation of active methylol groups formed upon the decomposition of the parent taurolidine. The active moieties of the taurolidine molecule are methylol-containing breakdown metabolites which react with the cell wall of the bacteria as well as with primary amino groups of endotoxins and exotoxins. Three methylol metabolites are generated from each molecule of taurolidine and the intermediate metabolites and catabolic molecular fragments are presented in FIG. 6.

Taurolidine inhibited the growth of all cell lines evaluated with $IC_{50}$s ranging from 9.6–45 μM. Cell lines examined included Murine fibroblasts (NIH-3T3); Ovary (PA-1, SKOV-3); Prostate (DU145, DU145/CR, PC3, LNCaP); Brain (U251, U251/MDR, T98G); Colon (HT29, HCT8, HCT15); Lung (HI 57, A549, H596); Mesothelioma (REN, LRK); Melanoma (B16-F10; MNT-1); Breast (MCF7); Non adherent cells (SPI, Daudi, HL60, CCL155). In every tumor cell line evaluated, taurolidine effectively inhibited tumor cell growth. Taurolidine has now been found to kill at least 28 different human tumor cell lines including ovarian, breast, brain, colon, prostate, urinary bladder and lung tumors, as well as melanomas, mesotheliomas, laryngeal carcinomas, leukemias, and lymphomas. In addition, multiple-drug resistant glioma cells and myelodysplastic syndrome cells (a precancerous cell type) were killed by taurolidine. inhibition of tumor growth and induction of tumor cell death occur at taurolidine concentrations significantly lower than those required for antibacterial or antiadhesive activity. Taurine compounds are useful to inhibit tumor cell growth and/or induce apoptotic cell death in the same or similar clinical situations in which taurolidine is used. The compounds are optionally combined with other chemotherapeutic agents.

The compounds described herein are toxic to tumor cells (but not normal non-tumor cells) but do not contain or generate methylol. Apoptosis of tumor cells is induced after contacting the tumor cell with an incubation with a taurine compound.

Figure 6:
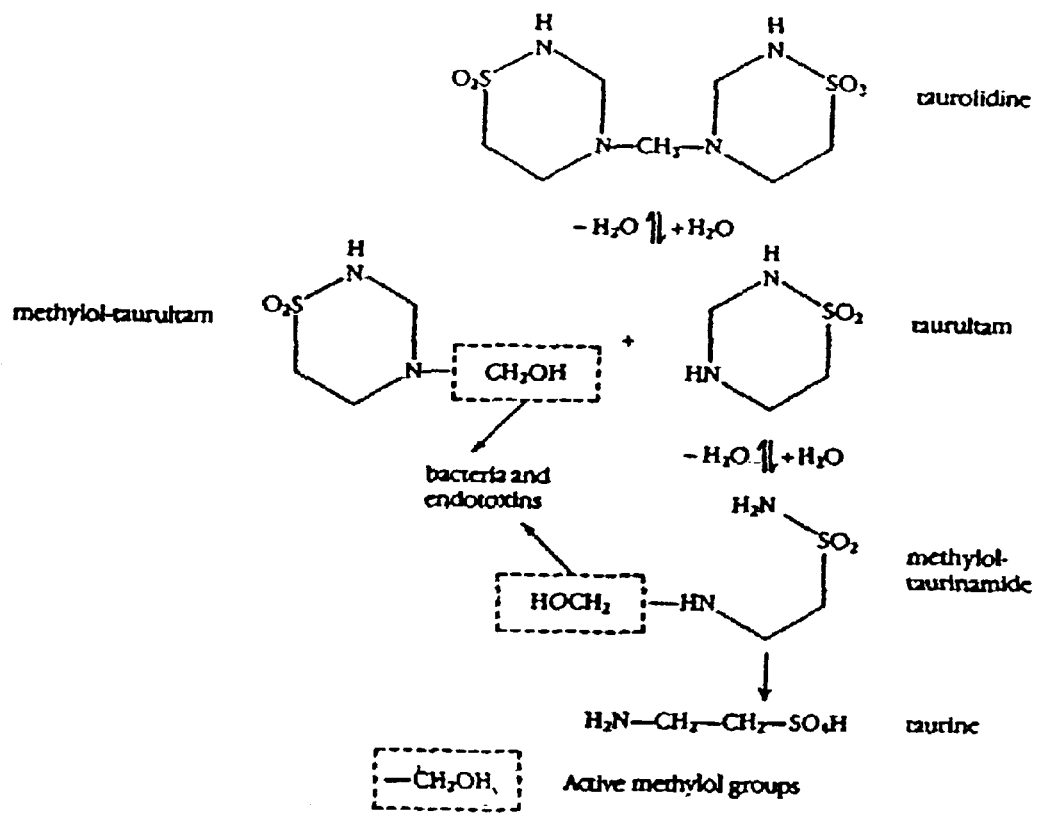
FIG. 6 is a diagram of taurolidine metabolism.

Taurolidine is very unstable in solution and spontaneously decomposes into the fragments (FIG. 6). In contrast, the compounds described herein are stable do not break down under similar conditions. The prolonged stability is an advantage over taurolidine.

Taurine was used as a molecular template for the generation of a series of derivative compounds containing the S—C—C—N taurine moiety. The stable taurine compounds do not contain or generate methylol groups and are stable in aqueous solution Therapeutic Administration An effective amount of a taurine compound is preferably from about 0.1 mg/kg to about 750 mg/kg. Higher doses may be administered without deleterious side effects. Effective doses vary, as recognized by those skilled in the art, depending on route of administration, excipient usage, and coadministration with other therapeutic treatments including use of other antitumor agents (e.g., an antimetabolite, a purine or pyrimidine analogue, an alkylating agent crosslinking agent, intercalating agent, or an antibiotic) and radiation therapy.

A therapeutic regimen is carried out by identifying a mammal, e.g., a human patient suffering from (or at risk of developing) a cancer or metastases using standard methods. For example, the taurine compound is administered to an individual diagnosed with a cancer (e.g., acute myeloid leukemia) or an individual diagnosed with a precancerous condition (e.g., myelodysplasia which may progress to acute myeloid leukemia). The pharmaceutical compound is to administered to such an individual using methods known in the art. Preferably, the compound is administered orally, topically or parenterally, e.g., subcutaneously, intraperitoneally, intramuscularly, and intravenously. For example, ovarian cancer is treated by intraperitoneal lavage using a pharmaceutically-acceptable solution of a taurine compound. The compound is administered prophylactically, after the detection of a recurring tumor, or at the time of surgery. The compound may be formulated as a component of a cocktail of chemotherapeutic drugs to treat a primary ovarian cancer or to prevent recurring tumors. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

A taurine compound is formulated into compositions for other routes of administration utilizing conventional methods. For example, it can be formulated in a capsule or a tablet for oral administration. Capsules may contain any standard pharmaceutically acceptable materials such as gelatin or cellulose. Tablets may be formulated in accordance with conventional procedures by compressing mixtures of a taurine compound with a solid carrier and a lubricant. Examples of solid carriers include starch and sugar bentonite. The compound is administered in the form of a hard shell tablet or a capsule containing a binder, e.g., lactose or mannitol, a conventional filler, and a tableting agent. Other formulations include an ointment, paste, spray, patch, cream, gel, resorbable sponge, or foam. Such formulations are produced using methods well known in the art.

Taurine compounds such as β-Azidoethanesulfonyl azide are effective upon direct contact of the compound with the cancer cell. Accordingly, the compound is administered topically. For example, to treat urinary bladder carcinoma, the compound is administered to the bladder using methods well known in the art, e.g., using a catheter to inflate the bladder with a solution containing the taurine compound for at least ten minutes. For example, the bladder is instilled with a solution of β-Azidoethanesulfonyl azide, and the solution allowed to remain in the bladder for 30 minutes to 2 hours. For treatment of skin malignancies such as basal cell carcinomas, a cream or ointment is applied to the area of skin affected by the tumor. Tumor cells in the liver (e.g., a primary tumor or liver metastases originating from primary tumor elsewhere in the body such as the colon or breast) are treated by infusing into the liver vasculature a solution containing a taurine compound. Alternatively, the compounds are administered by implanting (either directly into an organ such as the liver or subcutaneously) a solid or resorbable matrix which slowly releases the compound into adjacent and surrounding tissues of the subject. Implantation of a drug-loaded matrix directly into the liver effectively destroys tumor cells in the liver, while healthy liver tissue rapidly detoxifies any residual chemotherapeutic agent.

For treatment of cancers of the CNS such as glioblastomas, the compound is systemically administered or locally administered directly into CNS tissue. The compound is administered intravenously or intrathecally (i.e., by direct infusion into the cerebrospinal fluid). For local administration, a compound-impregnated wafer or resorbable sponge is placed in direct contact with CNS tissue. A biodegradable polymer implant such as a GLIADEL™ wafer is placed at the tumor site, e.g., after surgical removal of a tumor mass. A biodegradable polymer such as a polyanhydride matrix, e.g., a copolymer of poly (carboxy pbenoxy propane):sebacic acid in a 20:80 molar ratio, is mixed with a therapeutic agent, e.g., a taurine compound, and shaped into a desired form. Alternatively, an aqueous solution or microsphere formulation of the therapeutic agent is sprayed onto the surface of the wafer prior to implantation. The compound or mixture of compounds is slowly released in vivo by diffusion of the drug from the wafer and erosion of the polymer matrix. A taurine compound such as β-Azidoethanesulfonyl azide may be coadministered with other chemotherapeutic agents such as carmustine (BCNU).

The compound is infused into the brain or cerebrospinal fluid using known methods. For example, a burr hole ring with a catheter (for use as an injection port) is positioned to engage the skull at a burr hole drilled into the skull. A fluid reservoir connected to the catheter is accessed by a needle or stylet inserted through a septum positioned over the top of the burr hole ring. A catheter assembly (e.g., an assembly described in U.S. Pat. No. 5,954,687) provides a fluid flow path suitable for the transfer of fluids to or from selected location at, near or within the brain to allow administration of the drug over a period of time.

The compounds are also used to purge a sample of bone marrow cells of cancer cells which may contaminate the sample. Bone marrow cells are derived from a mammalian donor using standard methods. The cells are treated by contacting them with a taurine compound in vitro to eliminate contaminating tumor cells. After washing the treated cells, the treated bone marrow cell preparation is administered to a mammalian recipient to reconstitute the immune system of the recipient.

Similarly, a population of peripheral blood mononuclear cells is purged of tumor cells. Peripheral blood may be used as a source of stem cells, e.g., hematopoetic stem cells, for repopulating the immune system of a cancer patient following chemotherapy or radiation therapy. In some cases (e.g., patients with a myeloma or breast cancer), using peripheral blood as a source of stem cells is preferable to using bone marrow because the peripheral blood may be less contaminated with tumor cells. Peripheral blood mononuclear cells are obtained from an individual using standard methods, e.g., venipuncture or plasmapheresis. The cells are treated with a taurine compound, such as β-Azidoethanesulfonyl azide, in vitro or ex vivo to kill contaminating tumor cells. The cells are washed and infused into a recipient individual. Optionally, the cells are cultured to expand a desired cell type.

Cytotoxicity of Taurine Compounds

Taurine compounds are synthesized using methods known in the art. The taurine compounds differ from naturally-occurring taurine by the nature of the substituent groups.

The cytotoxic activity of β-Azidoethanesulfonyl azide and other taurine compounds is evaluated in vitro against the growth of a variety of human cancer cell lines as well as "normal" NIH 3T3 fibroblasts and found to induce apoptotic cytotoxicity. The neoplastic cell lines tested include standard tumor cell lines, e.g., PA1 human ovarian cell line, SKOV3 human ovarian cell line, HT29 human colon tumor cell line, DU145 human prostate tumor cell line, U251 human glioblastoma cell line, U251-MDR human glioblastoma cell line transfected with DNA encoding MDR, T98G human glioblastoma cell line, SP-1 human leukemia cell line, and Daudi human leukemia cell line. Increased cell death in the presence of the compound compared to the level in the absence of the compound indicates that the compound has antineoplastic activity.

Apoptotic death is distinguished from death by other mechanisms using methods known in the art. One indication of the induction of apoptosis is the cleavage of the protein poly (ADP-ribose) polymerase (PARP) by cellular caspases. Western-blot based studies are carried out to determine if exposure to a taurine compound results in PARP cleavage.

Apoptosis is also detected using known methods such as determination of caspase activation, bax/bcl12 ratios and fas and fas-I interactions. Other methods of distinguishing between apoptosis and necrosis (e.g., a fluorescence-based method described in U.S. Pat. No. No. 5,976,822) are used to determine the mechanism of death or the dose at which a taurine compound induces apoptosis compared to necrosis.

The antitumor activity of a compound is also evaluated using a standard MTS colorimetric assay. Results obtained with various types of tumor cells (primary cells or cell lines) are compared with those obtained by using normal cells. Viability of the cells in each cell line is estimated by measuring the cellular conversion of a tetrazolium salt after incubating the cells in a solution containing a test compound in a 96 well plate. $IC_{50}$ values obtained using the identical test compound on normal cells and cells of a particular tumor cell line are compared and their ratio ($IC_{50}$ normal cell/$IC_{50}$ cancer cell) indicates the cancer selectivity of the test compound. An increase in the $IC_{50}$ normal cell/$IC_{50}$ cancer cell ratio reflects a higher selectivity of the test compound to kill the cancer cell.

Antitumor activity of a compound is also evaluated in vivo using, e.g., a tumor xenograft regression assay. For example, animals bearing established tumors are treated with a test compound for a three-week period. The growth of the tumors and the general health of the animal are monitored during the three-week treatment and for two more weeks after treatment to determine if tumor regrowth occurs. The antineoplastic activity of a taurine compound is determined in athymic (nude) mice bearing advanced and/or metastatic xenografts. Single and multiple dose regimens of taurolidine are evaluated in athymic (nude) mice. Upon identification of dose regiments, antineoplastic activity is assessed in athymic (nude) mice bearing xenografts of human cancer cells, e.g., ovarian, prostate, colon, pancreatic, breast and glioma tumors.

Treatment of Leukemias and Lymphomas

The compounds described herein are assayed for use in treating non-anchorage-dependent tumor cell types such as lymphomas or leukemias. Two different non-anchorage-dependent tumor cell lines (a human Burkitt's lymphoma cell line, and a Daudi cell line), and precancerous cell line (a human myelodysplastic cell line) are grown in suspension culture. After exposing the tumor cells to 10–20 μM of a taurine compound for 72 hours, cell viability is assessed. Similar experiments are performed by exposing myelodysplastic cells to a taurine compound.

Treatment of Ovarian Cancer

Over 80% of patients diagnosed with ovarian cancer experience recurrent tumors after therapeutic intervention for the primary tumor. Even a 5% response rate, e.g., a 5% reduction in tumor growth, confers a clinical benefit. Response rate is defined as a reduction in tumor size or in the number of metastatic foci. For example, a reduction in tumor size is determined by detecting a decrease in the size of the largest neoplastic lesion, e.g., by sonogram or by measurement using a caliper.

A standard mouse model of ovarian cancer is used to study the effect of taurine compounds on recurrent ovarian cancer. Holland Sprague-Dawley mice are injected with $5 \times 10^6$ tumor cells (e.g., SKOV3 human ovarian tumor cell line) to mimic a condition of advanced ovarian cancer. The compound is administered by intraperitoneal lavage 5 days later. For example, the compound is administered 3 times a day for 4 days at a dose of 30 mg/day. A reduction in ovarian tumor burden or recurrence of tumors in treated animals compared to untreated animals indicates that the compound inhibits tumor cell growth and is useful as an antineoplastic agent.

Treatment of Drug Resistant Tumors

The ability of compounds to kill tumor cells which are refractory to cytotoxicity by other known chemotherapeutic agents is assessed. Glioblastoma cells are transfected with a gene encoding multiple drug resistance (MDR). The transfected cells are typically 100–1000 times resistant to standard chemotherapeutic agents, e.g., adriamycin. A reduction in tumor burden or recurrence of tumors in treated animals compared to untreated animals indicates that the compound inhibits tumor cell growth via a mechanism that differs from that of standard chemotherapeutic agents. Accordingly, combination therapy in which a taurine compound is administered before, after, or together with another chemotherapeutic agent (e.g., an antimetabolite, a tumor-specific monoclonal antibody, or anti-angiogenic agent) is likely to result in an improved clinical outcome of patients suffering from a malignant condition characterized by a mixed population of tumor cells (e.g., those which are killed by standard chemotherapeutic agents and those which are MDR).

EXAMPLE 1

Tumor Cell Growth Inhibition by Stable Taurine Compounds

Tumor cell growth inhibitory activity experiments were carried out in an art recognized cell line model for human cancers, PA1 human ovarian tumor cells.

The compounds to be tested were formulates as follows. A 10 mM stock solution of β-Azidoethanesulfonyl azide (BC-701) was generated. The BC-701 solution was diluted in 100% ethanol to achieve a concentration of 100 mM and then diluted in high glucose DMEM to achieve a final concentration of 10 nM. Thereafter, all drug solutions were sterilized by passing through a 0.22 μm syringe filter (Costar Corp.) and stored at −20° C. until use.

Cells were cultured using standard methods. Stock culture of PA1 cells were harvested and suspended by incubation in a standard 5× trypsin solution (GIBCO-BRL, Grand Island, N.Y.) for 5 minutes at 37° C. Thereafter, the harvested cells were resuspended in high glucose DMEM containing 10% fetal bovine serum (FBS) to achieve a cell density of approximately $1.0 \times 10^4$ cell/ml. Two ml of this cell suspension was added into each well of a 12 well disposable cell culture plate (Falcon/Becton Dickinson Labware, New Jersey) that contained 2 ml of tissue culture medium plus 10% FBS. Twenty-four hours later, BC-701 was added to each well to achieve final concentrations ranging from 5 $\mu$M to 100 $\mu$M. In control cultures, the test drug solution was replaced with an appropriate volume of a mixture of 10% ethanol in media. Seventy two hours later, all cells were harvested by trypsinization and cell number determined by electronic counting (Coulter Counter, Model ZM, Florida). In each experiment, all conditions were carried out in duplicate and each experiment was repeated a minimum of two times.

The results of these studies are summarized in Table 1. Cells were seeded at 1×10$^4$ cells in each well of a 12 well culture flask. Twenty-four hours later, BC-701 was added at concentrations of 5–100 $\mu$M. After 3 d, cells were harvested by trypsinization and cell number determined electronically. Cell growth inhibition was determined by comparison to control cultures. The IC$_{50}$ was calculated as the concentration required to inhibit cell number by 50%. The IC$_{50}$ value of BC-701 represents the mean +SE of 4 determinations. These results indicate that BC-701, an taurine compound that does not contain a methylol group and can not form such a functional group, has potent cytotoxic activity and is useful as an antineoplastic agent.

TABLE 1

The effect of BC-701 on the growth of human ovarian tumor cells.

| Compound | IC$_{50}$ ($\mu$M) |
|---|---|
| Taurolidine | 11.4 ± 1.8 |
| BC701 | 4.9 ± 2.3 |

EXAMPLE 2

Mechanism of Cytotoxic Activity

A mechanistic evaluation of the cytotoxic activity of taurolidine and taurine compounds was carried out in DU-145 human prostate tumor cells. This cell line was obtained from the American Type Culture Collection (ATCC; ATCC Designation No. HTB-81). Cells were maintained under standard cell culture conditions using standard tissue culture media, e.g., RPMI 1640 medium containing 10% FBS at 37 o in a humidified incubator in an atmosphere of 5% $CO_2$. Under these growth conditions, the doubling time of this cell line was approximately 24 h.

Flow cytometry studies were carried out as follows. One×10$^6$ cells were incubated for 24 h in medium containing serum. Twenty-four hours later, taurolidine or BC-701 was added in a volume of 40 $\mu$l to achieve a final concentration of 50 $\mu$M. Control cultures were incubated in media containing 40 $\mu$l of 5% Kollidon 17PF alone. Twenty-four h later, all cells were harvested by trypsinization and prepared for cytofluorometric analysis. Harvested cells were resuspended in ice cold phosphate-buffered saline at a final cell density of 2×10$^6$ cells/ml. The cells then were stained for 30 min at room temperature in the dark with a solution of 0.05 mg/ml propidium iodide, 0.6% Igepal, and 1% sodium citrate. Flow cytometry was performed by FACScan (Becton Dickinson, Plymouth, England) using the ModFit LT program (Becton Dickinson). Statistical analysis was performed with the Kruskal Wallis non-parametric ANOVA test followed by Dunn's multiple comparisons test using Instat (FIGS. 1A–B and 2A–B).

Cell cycle data is shown in FIGS. 1A–B and 2A–B. The large light grey peak in the sub-G0/G1 region represents DNA fragmentation associated with the progression of apoptosis. Statistical analysis of peak area is contained in the right-hand script and is denoted as "Apoptosis". This analysis revealed greater % apoptosis in BC-701-treated cells compared to taurolidine-treated cells. For example, 12.27% apoptosis was detected in taurolidine-treated cells, whereas 38% apoptosis was detected in cell populations contacted with BC-701. The level of apoptosis induced by BC-701 was at least 10% greater than that observed in taurolidine-treated cells. The data indicated that the level of apoptosis detected in cells treated with a taurine compound such as BC-701 was greater than 2-fold (e.g., 3-fold or more) the level detected in cell populations treated with taurolidine.

Western-blot analysis were also carried out to evaluate the mechanism of cytotoxicity of taurolidine and taurine compounds. Two×10$^6$ cells were seeded into separate 75 cm$^2$ tissue culture flasks containing 20 ml of medium plus serum. Twenty-four hours later taurolidine or BC-701was added at a concentrations of 50 $\mu$M. Twelve h after the addition of taurolidine or BC-701, cells were harvested, cell number determined, and aliquots containing an equal cell number were generated from each exposure condition. Total proteins from whole cell lysates generated from these aliquots were separated by SDS-PAGE and electrotransferred to nitrocellulose filters.

Induction of apoptosis was evaluated by detecting the cleavage of PARP by cellular caspases as described above. Filters were processed and probed with appropriate antibodies to detect PARP and procaspase 8a/b by conventional methods. The resulting protein-antibody complexes were visualized by chemiluminescence techniques (FIG. 3). The parent 115 kD molecule of PARP is converted to the 85 kD fragment as a result of the apoptotic process, and procaspase 8 is converted to caspase 8 early in the apoptotic process. Reduced expression of procaspase 8a/b and appearance of an 85 kDa fragment indicate apoptotic death.

The flow cytometric data shown in FIGS. 1A–B and 2A–B and the Western blot data shown in FIG. 3 indicate that taurine compounds, e.g., BC-701, induce apoptotic death of tumor cells. The data also indicate that taurine compounds described herein, e.g., BC-701, are more potent cytotoxic agents and exert cytotoxity more rapidly compared to taurolidine.

EXAMPLE 3

Bacterial Cell Growth Inhibition

A 5 mM stock solution of β-Azidoethanesulfonyl azide (BC-701) was generated as described in Example 1, with the exception that final dilutions were made in LB growth medium (Gibco) for use in these studies. Specifically, BC-701 was diluted in 100% ethanol to achieve a concentration of 100 mM and then diluted in LB bacterial cell growth medium (Gibco) to achieve a final concentration of 5 mM. Thereafter, all drug solutions were sterilized by passing through a 0.22 $\mu$m syringe filter (Costar Corp.) and stored at −20° C. until use.

Stock cultures of *Escherichia coli* bacterial cells (Carolina Biological Supply Company) in 5 ml of LB were maintained at 40 C. Approximately 2 days before the initiation of experiments, 100 $\mu$l of stock bacterial culture solution was added to 10 ml of sterile LB and placed in a 37° C. incubator. To initiate experiments to assess the ability of taurine compounds to inhibit bacterial cell growth, six sterile culture flasks, each containing LB media, an aliquot of *E. coli* cells, and experimental drug (concentrations≦1000 $\mu$M) were generated. Immediately thereafter, the relative optical density at a wavelength of 600 nm (vs. a sample of LB without bacterial cells) was determined on an Ultrospec Model 2000 recording spectrophotometer (Pharmacia Biotech Inc.). At hourly intervals thereafter, the relative optical density of each flask was determined according to the method outlined above. An increasing optical density as a function of time is a reflection of increased media turbity and reflects increased bacterial cell number. This method was employed to assess the bacterial cell growth inhibitory activity of BC-701 and taurolidine.

Figure 1A:
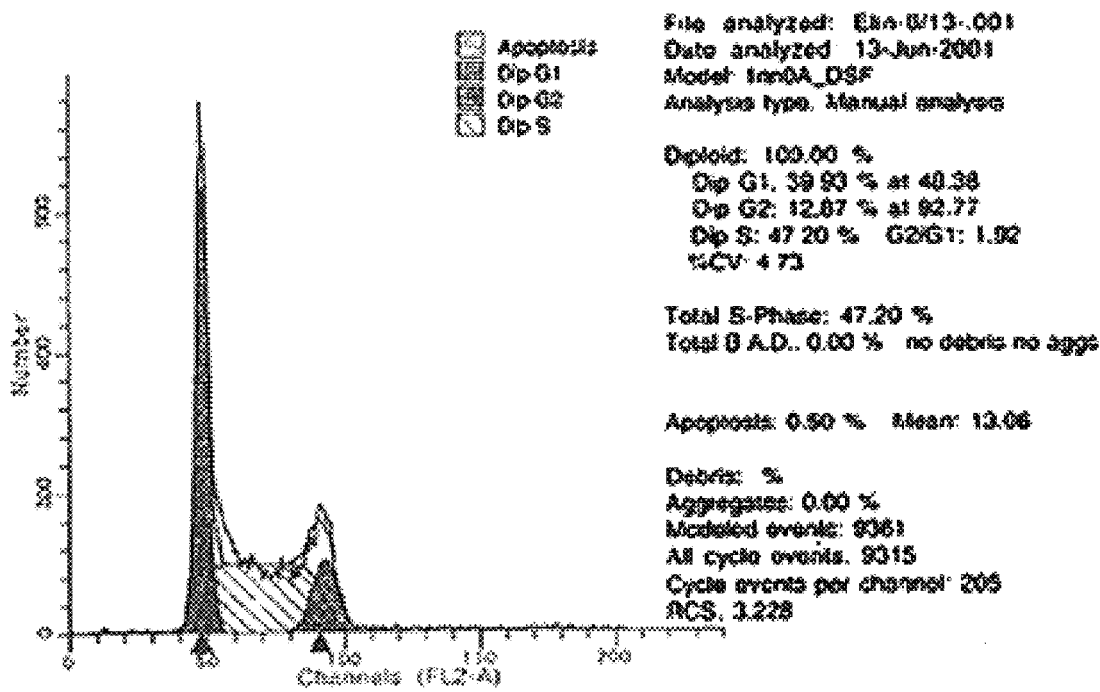
FIGS. 1A–B are histograms of a cytofluorometric assay of tumor cells. Human prostate tumor cells were contacted with 50 μM taurolidine for 25 hours prior to analysis (FIG. 1B) or maintained in the absence of taurolidine for 24 hours as a control (FIG. 1A).
Figure 1B:
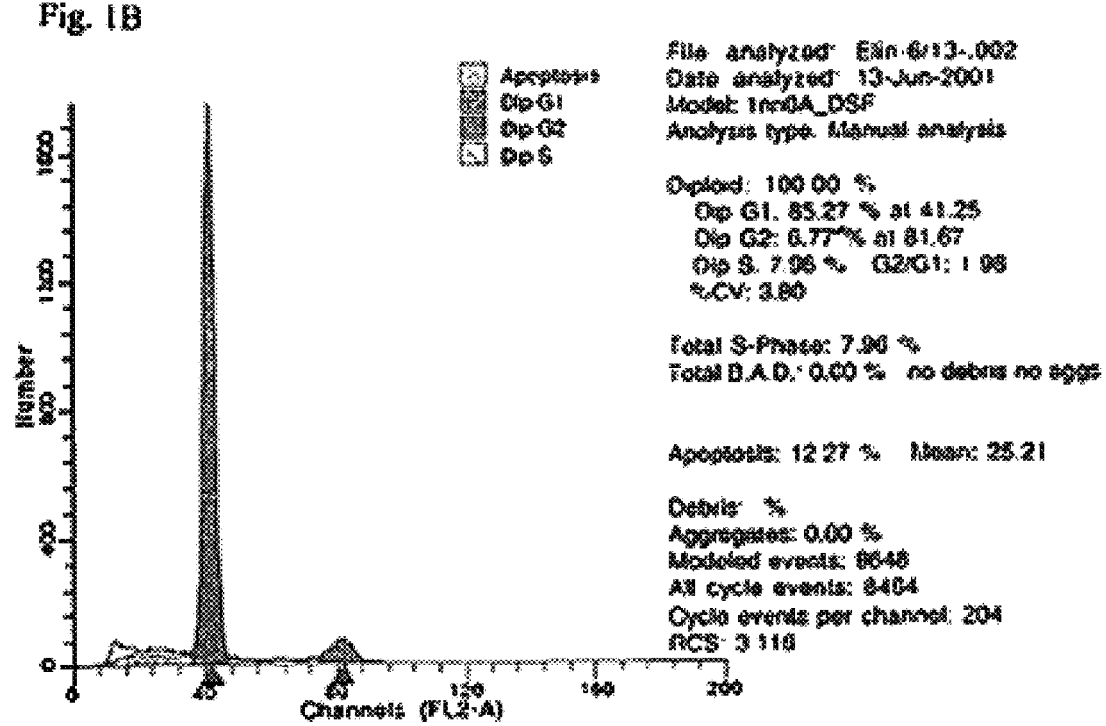
Figure 2A:
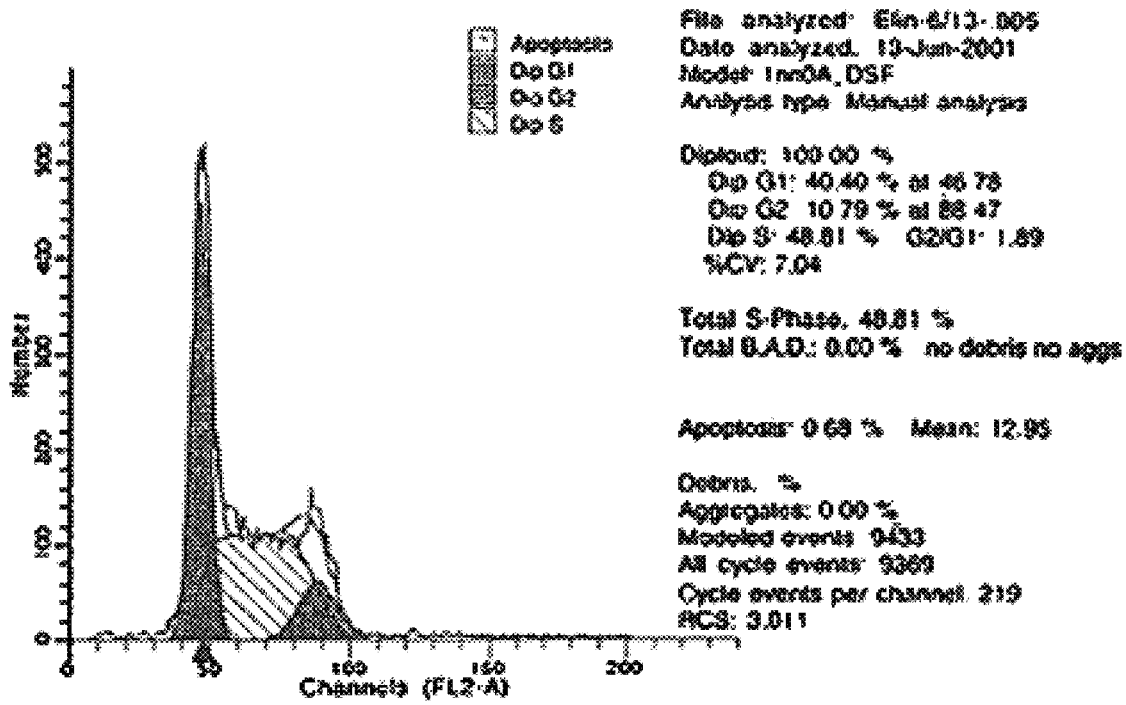
FIGS. 2A–B are histograms of a cytofluorometric assay of tumor cells. Human prostate tumor cells were contacted with 50 μM of β-Azideethanesulfonyl azide (BC-701) for 24 hours prior to analysis (FIG. 2B) or maintained in the absence of BC-701 for 24 hours as a control (FIG. 2A).
Figure 2B:
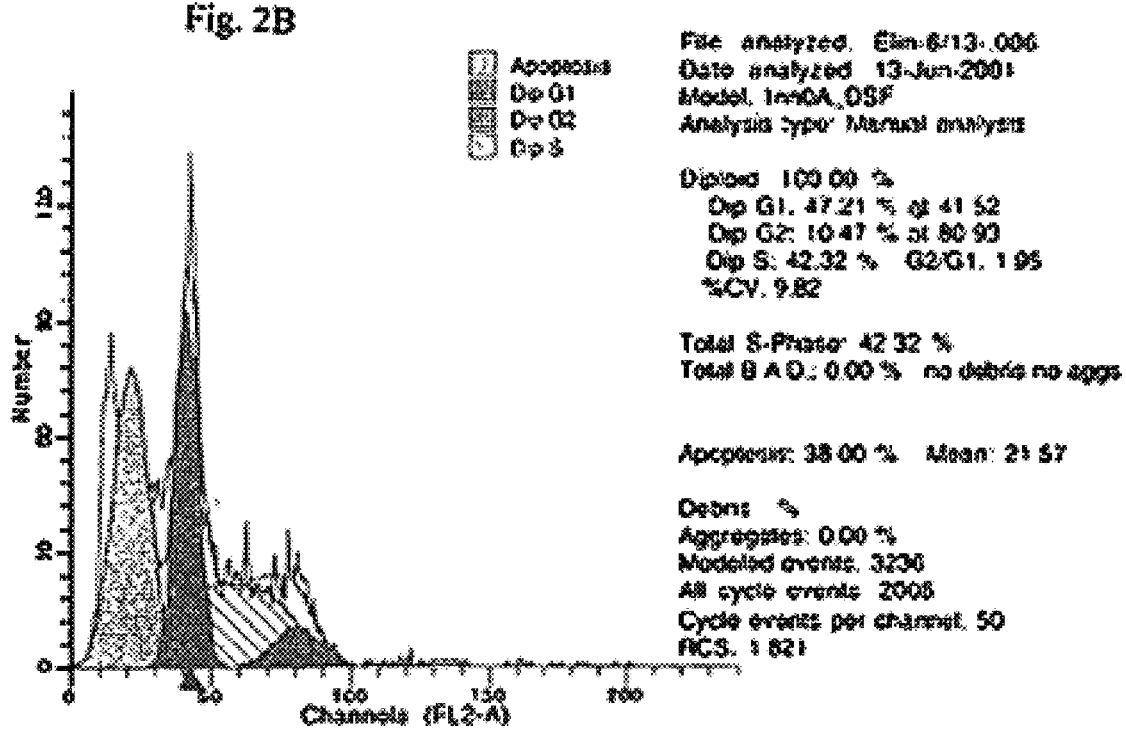
Figure 4:
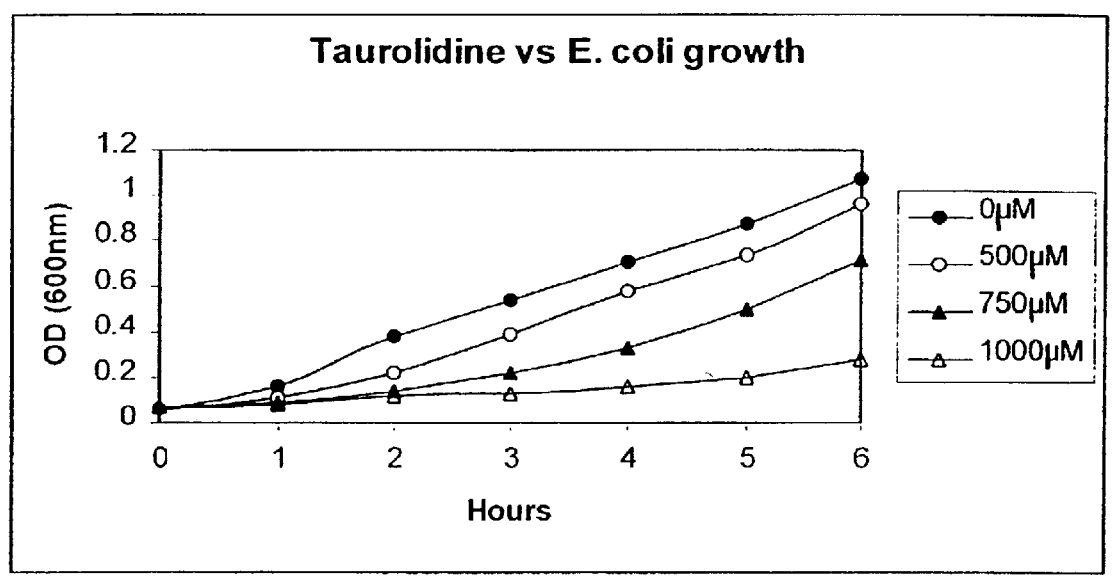
FIG. 4 is a graph showing the effect of exposure to various concentrations of taurolidine on *Eschericia coli* bacterial cell growth. Optical density (OD) was measured at hourly intervals, up to a 6 hour exposure.
Figure 5:
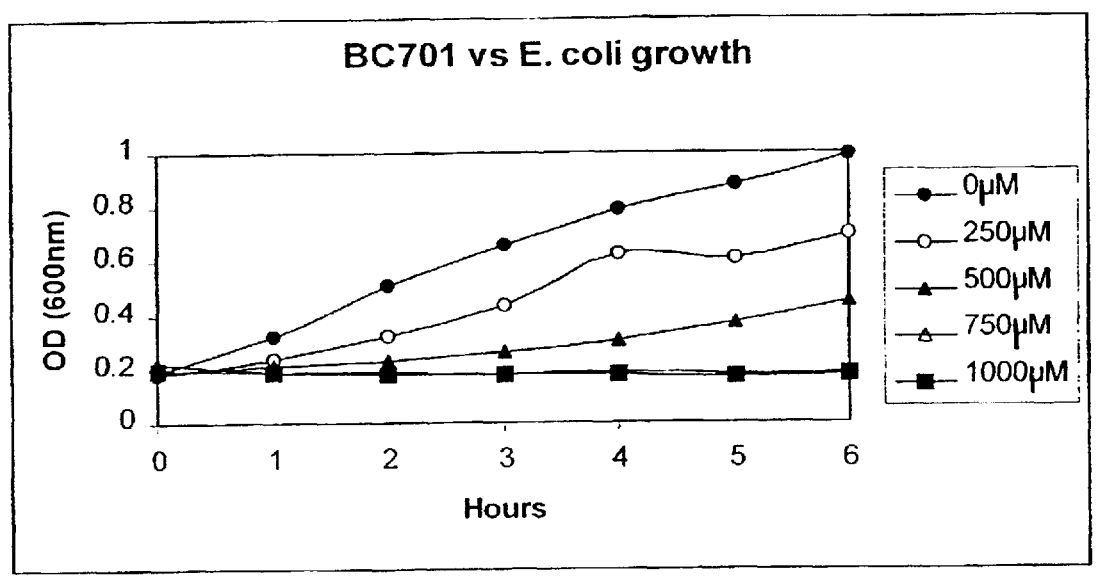
FIG. 5 is a graph showing the effect of exposure to various concentrations of β-Azidoethanesulfonyl azide (BC-701)on *Eschericia coli* bacterial cell growth. Optical density (OD) was measured at hourly intervals, up to a 6 hour exposure.

The results of these studies are summarized in FIGS. 4–5 (for taurolidine and β-Azidoethanesulfonyl azide, respectively). These results indicate that BC-701 possessed potent bacterial cell growth inhibitory activity. The level of antibacterial activity was comparable to that of taurolidine, and indicate that taurine compounds are useful as antibiotics.

Other embodiments are within the following claims.

What is claimed is:

1. A cytotoxic pharmaceutical composition comprising a pharmaceutically acceptable amount of a non-naturally occurring taurine compound having the formula $R_1$—$CH_2$—$CH_2$—$SO_2$—$R_2$, wherein $R_1$ and $R_2$ are azide, and a pharmaceutically acceptable carrier or excipient.

2. The pharmaceutical composition of claim 1, wherein said pharmaceutical composition is in the form of an ointment, paste, spray, patch, cream, gel, sponge or foam.

* * * * *